United States Patent
Yang

(10) Patent No.: US 9,566,011 B2
(45) Date of Patent: Feb. 14, 2017

(54) SYSTEMS AND METHODS FOR DIAGNOSING CARDIOVASCULAR CONDITIONS

(71) Applicant: UNIVERSITY OF SOUTH FLORIDA, Tampa, FL (US)

(72) Inventor: Hui Yang, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 14/421,012

(22) PCT Filed: Sep. 11, 2013

(86) PCT No.: PCT/US2013/059236
§ 371 (c)(1),
(2) Date: Feb. 11, 2015

(87) PCT Pub. No.: WO2014/043216
PCT Pub. Date: Mar. 20, 2014

(65) Prior Publication Data
US 2015/0216432 A1    Aug. 6, 2015

Related U.S. Application Data

(60) Provisional application No. 61/700,575, filed on Sep. 13, 2012.

(51) Int. Cl.
*A61B 5/04* (2006.01)
*A61B 5/00* (2006.01)
*A61B 5/0452* (2006.01)

(52) U.S. Cl.
CPC ....... *A61B 5/04011* (2013.01); *A61B 5/04012* (2013.01); *A61B 5/0452* (2013.01); *A61B 5/7246* (2013.01); *A61B 5/7264* (2013.01); *A61B 5/7267* (2013.01)

(58) Field of Classification Search
CPC ..... A61B 5/02; A61B 5/0402; A61B 5/04011; A61B 5/0452; G06K 9/62; G06T 7/00
USPC ....................................................... 600/512
See application file for complete search history.

(56) References Cited

U.S. PATENT DOCUMENTS

| | | | |
|---|---|---|---|
| 2003/0083587 A1* | 5/2003 | Ferek-Petric | A61B 5/0464 600/512 |
| 2006/0258947 A1 | 11/2006 | Olson | |
| 2010/0098289 A1 | 4/2010 | Tognoli | |
| 2010/0104203 A1 | 4/2010 | Garakani | |
| 2010/0179446 A1 | 7/2010 | Bojovic | |

OTHER PUBLICATIONS

H. Yang, C. Kan†, G. Liu† and Y. Chen†, "Spatiotemporal differentiation of myocardial infarctions," IEEE Transactions on Automation Science and Engineering, vol. 10, No. 4, p. 938-947, 2013.

(Continued)

*Primary Examiner* — Christopher D Koharski
*Assistant Examiner* — Roland Dinga
(74) *Attorney, Agent, or Firm* — Thomas | Horstemeyer, LLP

(57) ABSTRACT

In one embodiment, a cardiovascular condition is diagnosed by recording a vectorcardiogram for a subject under evaluation, comparing the vectorcardiogram with vectorcardiograms of other subjects, and diagnosing the subject under evaluation based upon the comparison.

20 Claims, 10 Drawing Sheets

(56) References Cited

OTHER PUBLICATIONS

C. Kan, Y. Chen and H. Yang, "Mobile Sensing and Network Analytics for Realizing Smart Automated Systems towards Health Internet of Things," Proceedings of the 11th Annual IEEE Conference on Automation Science and Engineering (CASE), Aug. 24-28, 2015, Gothenberg, Sweden.
C. Kan and H. Yang, "Dynamic spatiotemporal warping for the detection and location of myocardial infarctions," Proceedings of the 8th Annual IEEE Conference on Automation Science and Engineering (CASE), p. 1046-1051, Aug. 20, 2012, Seoul, Korea.
Hui Yang, et al., "Identification of myocardial infarction (MI) using spatio-temporal heart dynamics" Medical Engineering & Physics vol. 34, Issue 4,31 May 2012. See pp. 485-497.
International Search Report and Written Opinion, dated Dec. 27, 2013.

* cited by examiner

SYSTEMS AND METHODS FOR DIAGNOSING CARDIOVASCULAR CONDITIONS

CROSS-REFERENCE TO RELATED APPLICATION

This application is the 35 U.S.C. §371 national stage of, and claims priority to and the benefit of, PCT application PCT/US2013/059236, filed Sept. 11, 2013, which claims priority to and the benefit of U.S. Provisional Application No. 61/700,575, filed on Sep. 13, 2012, herein incorporated by reference in their entirety.

NOTICE OF GOVERNMENT-SPONSORED RESEARCH

This invention was made with Government support under grant/contract 1266331, awarded by the National Science Foundation (NSF). The Government has certain rights in the invention.

BACKGROUND

Myocardial infarction (MI), commonly known as a heart attack, is the leading cause of death in United States. MI occurs due to the occlusion of the coronary arteries. This results in insufficient blood and oxygen supply that lead to damaged cardiac muscle cells and trigger a disease-induced degradation process. The accurate diagnosis of MIs is critical for timely medical intervention and maintaining quality of life.

An electrocardiogram (ECG) contains dynamic information pertinent to space-time cardiac electrical activity. The ECG signal is a temporal recording of cardiac electrical signal that initiates at the sinoatrial (SA) node, is conducted in both atria, and is relayed through the atrioventricular (AV) node to further propagate through the bundle of His and Purkinje fibers to provide ventricular depolarization and repolarization. The ECG signal is typically plotted as a trace that is segmented into a P wave, a QRS complex, and a T wave. Each segment is closely associated with the specific physical activities of the heart chambers. For example, atrial depolarization (and systole) is represented by the P wave, ventricular depolarization (and systole) is represented by the QRS complex, and ventricular repolarization (and diastole) is represented by the T wave.

The time-domain ECG and its features (e.g., Q wave, QT interval, ST elevation or depression, T wave) are often used to identify cardiovascular conditions, such as MI. However, because the ECG trace is a time-domain projection of space-time cardiac electrical activity, the ECG trace diminishes important spatial information of cardiac pathological behaviors. Accordingly, critical medical decisions are made without having all of the relevant information as to the condition of the heart, especially in cases in which there is a lesion in initial stages of growth.

In view of the above discussion, it can be appreciated that it would be desirable to have a system and method for diagnosing cardiovascular conditions that fully account for both time- and space-domain information about cardiovascular function.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it would be desirable to have a system and method for diagnosing cardiovascular conditions that fully account for both time- and space-domain information about cardiovascular function. Disclosed herein are examples of such systems and methods. In some embodiments, 3-lead vectorcardiograms (VCGs) of multiple subjects are recorded and the spatiotemporal distances (dissimilarities) between the recordings are measured. The measurements can be incorporated into a dissimilarity matrix from which feature vectors can be extracted. The feature vectors can then be embedded in a high-dimensional space to form a network that preserves the distances between the recordings. Once the network has been formed, each recording, and subject, can be correlated with a particular cardiovascular condition, such as myocardial infarction (MI), if applicable.

In the following disclosure, various specific embodiments are described. It is to be understood that those embodiments are example implementations of the disclosed inventions and that alternative embodiments are possible. All such embodiments are intended to fall within the scope of this disclosure.

Multi-lead electrocardiogram (ECG) systems, such as 12-lead ECG systems, are widely used because medical doctors are accustomed to using them in clinical practice. It has been determined, however, that 3-lead VCGs can be linearly transformed into 12-lead ECGs. Thus, the information contained in a 12-lead ECG is redundant and all of the information that may be needed by a physician can be obtained from a 3-lead VCG. The 3-lead VCG monitors space-time cardiac electrical activity along three orthogonal X, Y, Z planes of the body, namely the frontal, transverse, and sagittal planes. Because MI can take place in different spatial locations of the heart (e.g., anterior and inferior), space-time cardiac electrical activity is often perturbed by the location of lesions in the heart.

Figure 1:
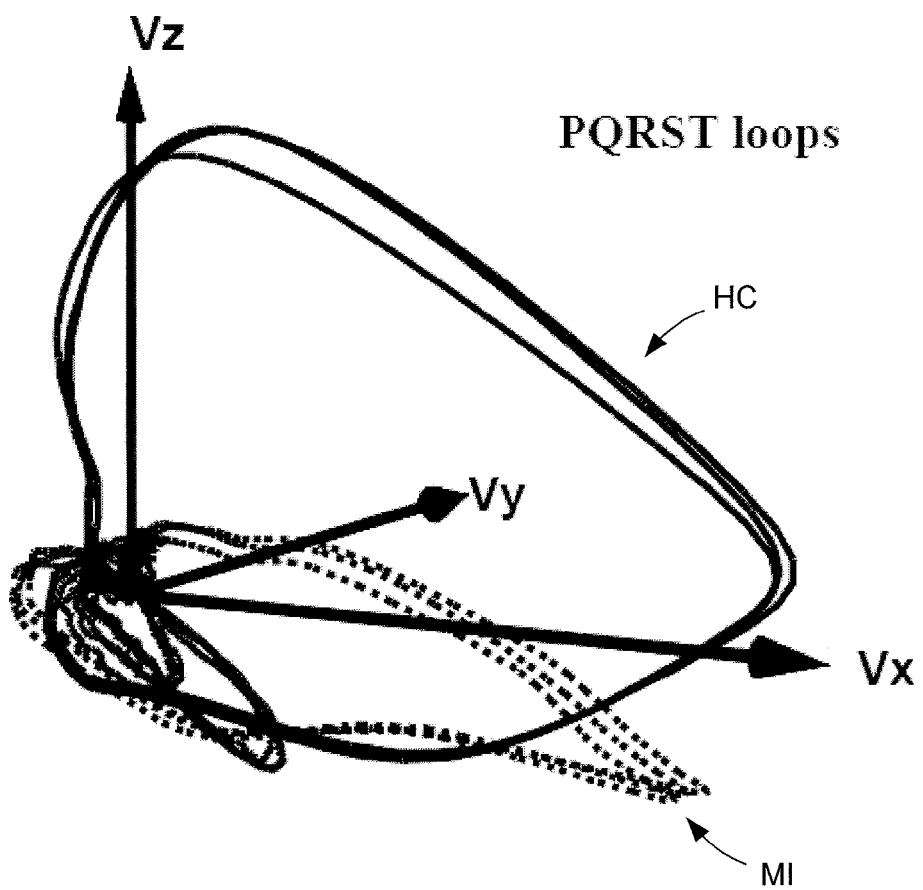
FIG. 1 is a graph that plots example 3-lead vectorcardiograms (VCGs) of space-time cardiac electrical activity for a healthy control (HC) subject and a myocardial infarction (MI) subject.

FIG. 1 illustrates example VCG trajectories. The trajectories are three-dimensional (3-D) plots of cardiac electrical activity. Each trajectory's path varies as a function of both time and space (as defined by an x, y, z coordinate system). In FIG. 1, the solid trajectories represent the VCG signals from a healthy control (HC) subject and the dashed trajectories are from an MI subject. As can be appreciated from the figure, the HC and MI recordings show vastly dissimilar cardiac electrical activity in space and time. Previous studies conducted by the inventors demonstrated that there are statistically significant differences in the spatiotemporal paths of cardiac electrical activity between healthy and diseased subjects. However, the spatiotemporal distances between the VCG signals of healthy and diseased subjects have not been quantitatively measured. In addition, these distances have never been utilized to identify the locations of cardiovascular conditions, such as MIs.

Figure 2A:
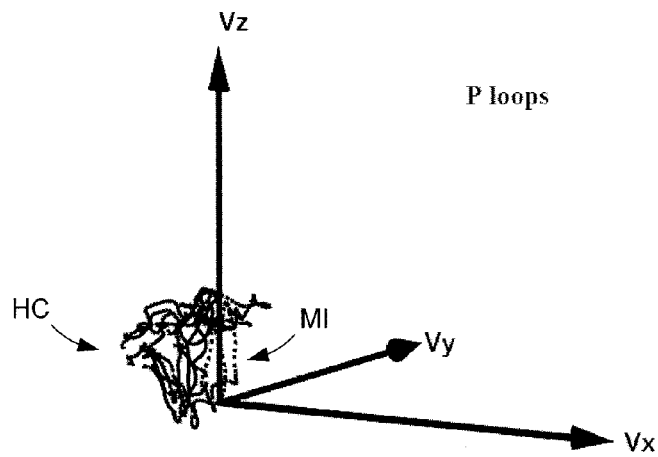
FIGS. 2A-2C are graphs that plot example segmented VCGs (P loops, QRS loops, and T loops, respectively) for HC and MI subjects.
Figure 2B:
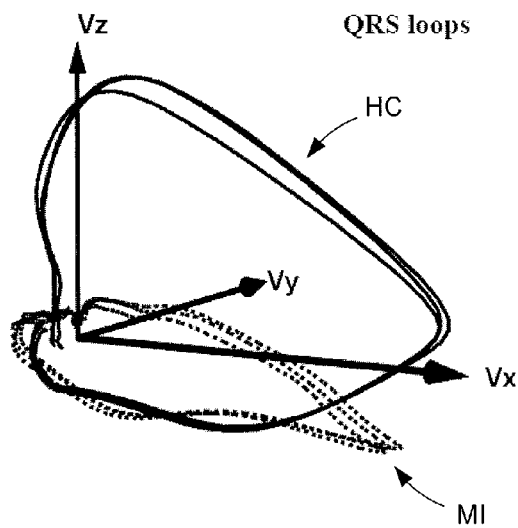
Figure 2C:
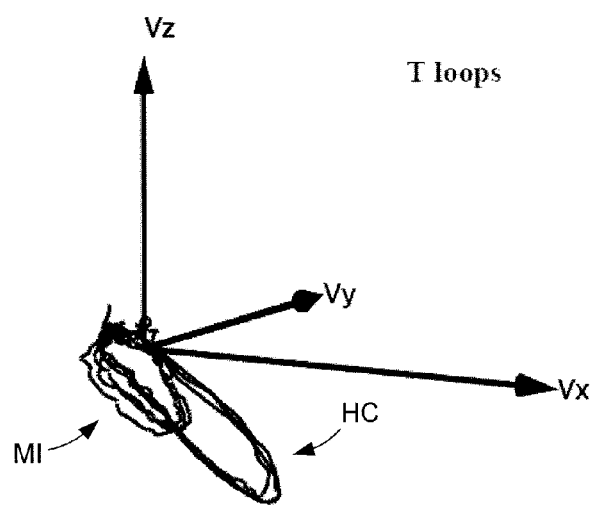

As shown in FIG. 2A, the P loops of the VCG signal are relatively close and visually entangled for both HC and MI subjects. Note that the P wave is pertinent to atrial depolarization. The QRS and T waves pertain to the ventricular depolarization and repolarization. Because MI commonly takes place in the ventricles, QRS and T waves are more often used to identify MI-related patterns than the P wave. As shown in FIGS. 2B and 2C, the QRS and T loops yield more significant differences between HC and MI subjects than the P wave. However, previous studies demonstrated that the MI can slow, or even block, the conduction from the atrium to the ventricles, thereby causing the variations of P waves. The space-time information from the VCG loops, as well as the segmented P, QRS, and T loops, can be exploited to differentiate the spatial locations of cardiovascular conditions, such as MIs. As described below, a warping approach can be used to quantify the dissimilarity of 3-lead spatiotemporal VCG signals and to diagnose cardiovascular conditions.

Figure 3:
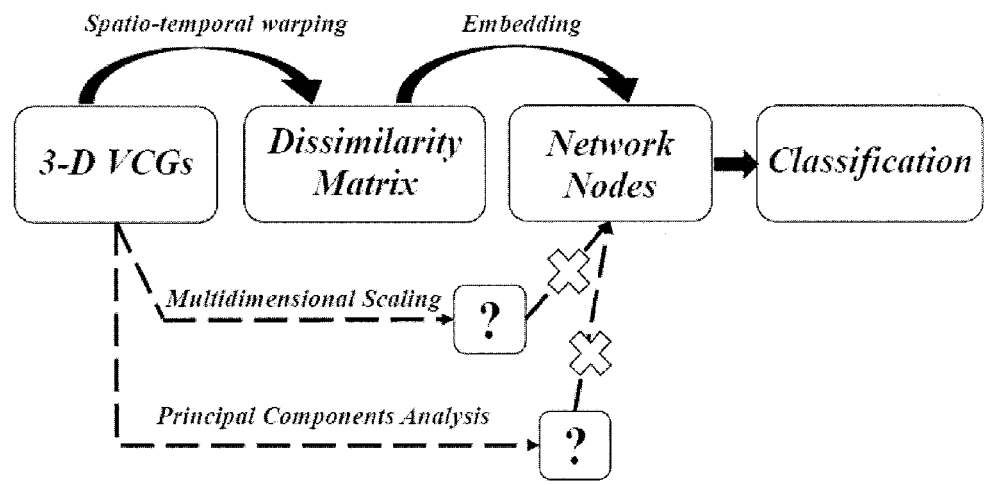
FIG. 3 is a flow diagram of an embodiment of a cardiovascular diagnosis methodology.
Figure 4:
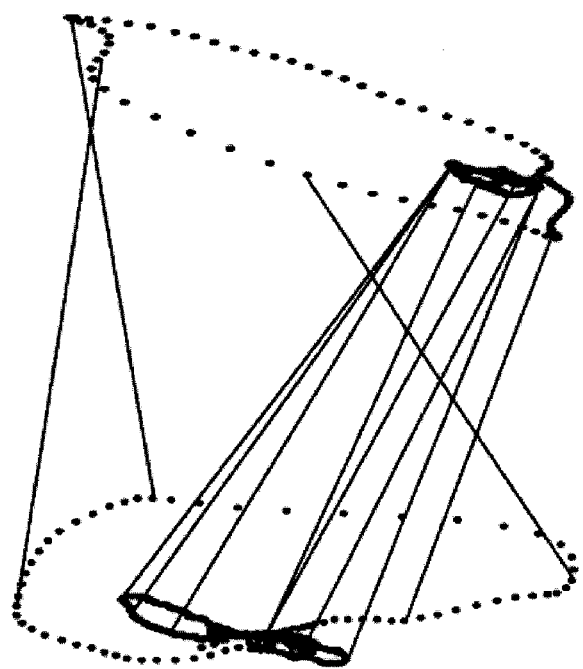
FIG. 4 is a graph that shows spatiotemporal alignment of 3-lead VCG signals.

The methodology used to make the cardiovascular diagnoses is schematized in FIG. 3. First, a dynamic spatiotemporal warping algorithm can be used to measure spatiotemporal dissimilarities between the entire 3-lead VCG signals (i.e., functional recordings). A matrix of global warping distances is then obtained. This matrix can be referred to as the global "dissimilarity" matrix. In addition, the 3-lead VCG signals can be segmented into P, QRS, and T loops to calculate three local dissimilarity matrices. Second, a feature embedding algorithm can be used to extract feature vectors from the one or more dissimilarity matrices. The functional recordings can be embedded as feature vectors in a high-dimensional space that preserves warping distances among the recordings. Third, classification models (e.g., a self-organizing map and logistic regression) can be used to correlate the patterns of warping features with the spatial locations of cardiovascular conditions, such as MIs.

This approach is vastly different from traditional methods in dimension reduction, such as multi-dimensional scaling (MDS) and principal component analysis (PCA). As shown in FIG. 3, the warping matrix bridges the gap between 3-lead VCG and feature vectors. As a result, each signal is embedded as a vector in high-dimensional space. If MDS or PCA are directly applied to 3-lead VCG, space-time pattern dissimilarity cannot be measured and embedded features cannot be achieved.

With reference back to FIG. 1, spatiotemporal dissimilarity is found between the functional recordings of 3-lead VCGs of MI and HC subjects. Quantification of such dissimilarity provides a great opportunity for the identification of cardiovascular conditions. However, it is challenging to measure the spatiotemporal dissimilarity between two functional signals in both space and time. Due to phase shift and discrete sampling, two VCG signals can be misaligned, e.g., both signals show a typical pattern and yet there are variations in shape, amplitude and phase between them. Therefore a new method is needed to measure the time-normalized spatial dissimilarity between 3-D functional signals.

Dynamic time warping (DTW) is used in speech recognition to measure the similarity between two time series. Previous works have shown that dynamic time warping methods efficiently handle the misalignment in time series by searching the optimal matching path. However, such approaches are limited to the warping of one-dimensional time series. The dissimilarity between two time series is characterized mainly in the time domain. As mentioned above, however, cardiac electrical signals are excited and propagated spatiotemporally, and disease-altered signal patterns are shown in both space and time.

Figure 5:
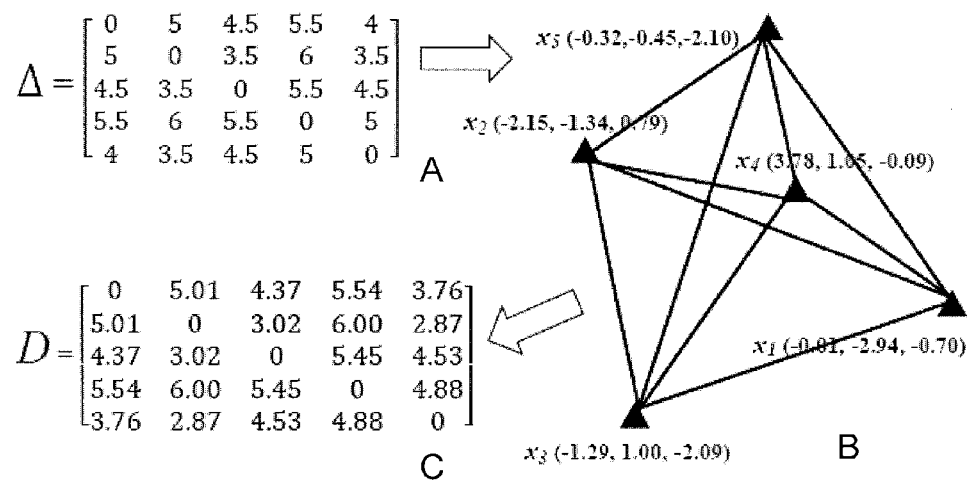
FIG. 5A is an example dissimilarity matrix.
FIG. 5B is an example reconstructed network and nodes in 3-D space resulting from spatiotemporal warping of the distances of the dissimilarity matrix of FIG. 5A.
FIG. 5C is a reconstructed dissimilarity matrix D obtained after creating the reconstructed network of FIG. 5B.

A novel dynamic spatiotemporal warping approach has been developed to measure the dissimilarities between space-time functional recordings. As shown in FIG. 5, P, QRS, and T loops are aligned respectively for two subjects in both space and time. Such an alignment is important to compare the corresponding electrical activity of heart chambers. For example, the ventricular depolarization (i.e., QRS loops) for two subjects are compared, as opposed to the incorrect comparison between atrial depolarization (P loops) from one subject and ventricular depolarization from the other subject.

Given two 3D VCG signals $\vec{v}_1(t)$ and $\vec{v}_2(t)$, the time-normalized spatial distance between $\vec{v}_1(t)$ and $\vec{v}_2(t)$ is calculated as $\Sigma_{(t_i,t_j) \in p} \|\vec{v}_1(t_i) - \vec{v}_2(t_j)\|$ by alignment p. The warping path p(i,j) connects (1, 1) and ($N_1$, $N_2$) in a two-dimensional square lattice as well as satisfies constraints such as monotonicity condition and step-size condition. To find the optimal path, an exhaustive search of alignment path is intractable and computationally expensive. However, this problem can be efficiently solved using dynamic programming (DP) methods. The DP algorithm, a spatiotemporal warping algorithm, is started at the initial condition: $g(1,1) = d(1,1) = \|\vec{v}_1(t_1) - \vec{v}_2(t_1)\|$ and the warping window $|i-j| < r$. The algorithm searches forward as:

$$g(i, j) = \min \begin{pmatrix} g(i, j-1) + d(i, j) \\ g(i-1, j-1) + d(i, j) \\ g(i-1, j) + d(i, j) \end{pmatrix} \qquad \text{[Equation 1]}$$

Finally, the time-normalized spatial distance is calculated as:

$$\Delta(\vec{v}_1, \vec{v}_2) = \frac{g(N_1, N_2)}{N_1 + N_2} \quad \text{[Equation 2]}$$

where $N_1$ and $N_2$ are the length of $\vec{v}_1(t)$ and $\vec{v}_2(t)$, respectively. The $\Delta(\vec{v}_1, \vec{v}_2)$ represents the spatiotemporal dissimilarity between two multi-dimensional functional recordings. Therefore, disease-altered characteristics of 3-lead VCG signals are obtained in the dissimilarity matrix.

It is noted that the dissimilarity matrix cannot by itself be used to provide features for the identification of disease properties in classification models. In addition, the measure of Euclidean distance is not directional and can mix distances that are equal in magnitude but aligned along different spatial directions. Accordingly, a novel method must be used to transform the dissimilarity matrix into feature vectors that preserve the warping distances among functional recordings. This method is a spatial embedding method that embeds the functional recordings as the points in a high-dimensional space. These points can be used as feature vectors that recover not only the dissimilarity matrix but also directional differences between the functional recordings. This problem is similar to a network problem, i.e., how to reconstruct the nodes' location in a high-dimensional space if the node-to-node dissimilarity matrix is known. As shown in FIG. 5, a network comprises a number of nodes that are connected by lines. Each node represents an individual component in the system (a patient VCG in this context) and the lines show the relationships (e.g., distances or causal relationships) between the nodes. As given in FIG. 5A, assume the dissimilarity matrix $\Delta$ for 5 nodes is known. If the network is reconstructed in 3-D space, this is analogous to optimally identifying the coordinate vector $x_i = (x_{i1}, x_{i2}, x_{i3})$, i=1, 2, . . . , 5 for 5 nodes that can preserve the dissimilarity matrix $\Delta$. As shown in FIG. 5B, all of the nodes and their connections preserve the dissimilarity matrix $\Delta$. A reconstructed dissimilarity matrix D comprises the pairwise distances between reconstructed nodes in the 3-D space (see FIG. 5C). This, in effect, is bridging from functional signals to the dissimilarity matrix to feature vectors (nodes in the network). The feature vectors will approximately preserve the dissimilarity matrix $\Delta$ between functional signals. This feature embedding method can be referred to as multi-dimensional scaling.

Let $\delta_{ij}$ denote the dissimilarity between $i^{th}$ and $j^{th}$ functional recordings in n×n dissimilarity matrix $\Delta$, $x_i$ and $x_j$ denote the $i^{th}$ and $j^{th}$ feature vectors in a high-dimensional space. Then, the objective function of the feature embedding algorithm is formulated as:

$$\min \sum_{i<j} (\|x_i - x_j\| - \delta_{ij}); i, j \in [1, n] \quad \text{[Equation 3]}$$

where $\|\cdot\|$ is the Euclidean norm. To solve this optimization problem, a Gram matrix B is firstly reconstructed from the n×n dissimilarity matrix $\Delta$:

$$B = -\frac{1}{2} H \Delta^{(2)} H \quad \text{[Equation 4]}$$

where the centering matrix $H = I - n^{-1} 11^T$ and 1 is a column vector with n ones. The $\Delta^{(2)}$ is a squared matrix and each element in $\Delta^{(2)}$ is $\delta_{ij}^2$ (i.e., the squares of $\delta_{ij}$ in the matrix $\Delta$). The element $b_{ij}$ in matrix B is:

$$b_{ij} = -\frac{1}{2}\left[\delta_{ij}^2 - \frac{1}{n}\sum_{k=1}^{n}\delta_{ik}^2 - \frac{1}{n}\sum_{k=1}^{n}\delta_{kj}^2 + \frac{1}{n^2}\sum_{g=1}^{n}\sum_{h=1}^{n}\delta_{gh}^2\right] \quad \text{[Equation 5]}$$

It is known that the Gram matrix B is defined as the scalar product $B = XX^T$, where the matrix X minimizes the aforementioned objective function. The Gram matrix B can be further decomposed as: $B = V\Lambda V^T = V\sqrt{\Lambda}\sqrt{\Lambda}V^T$ where $V = [v_1, v_2, \ldots, v_n]$ is a matrix of eigenvectors and $\Lambda = \text{diag}(\lambda_1, \lambda_2, \ldots, \lambda_n)$ is a diagonal matrix of eigenvalues. Then, the matrix of feature vectors is obtained as: $X = V\sqrt{\Lambda}$. The algorithm embeds each functional recording as a feature vector in the d-dimensional space (d=2, 3, 4 . . . ).

Figure 6:
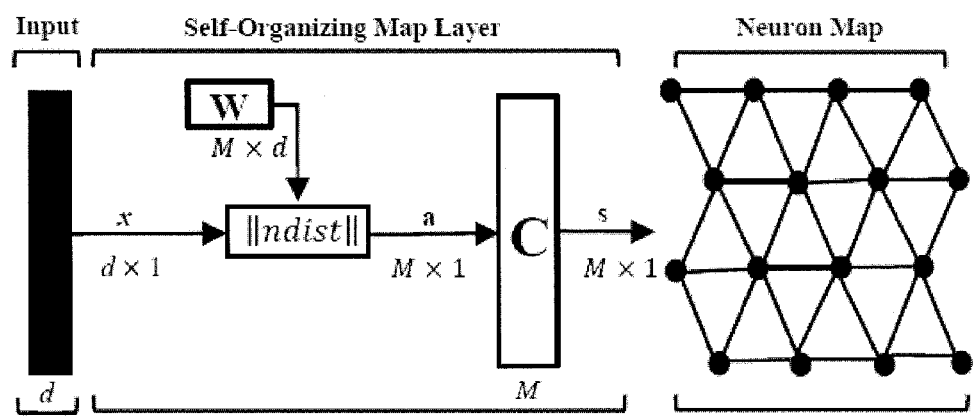
FIG. 6 is a diagram of an embodiment of a self-organizing map network structure.

At this point, classification models can be used to correlate the patterns of feature vectors with the spatial locations of cardiovascular conditions. In some embodiments, a self-organizing map (SOM) can be utilized to determine how self-organized patterns of feature vectors are correlated with the spatial locations of the conditions because SOMs can represent high-dimensional data in a low-dimensional map, preserve the topological relationship of the original data, and organize the data automatically according to the inherent structures. As shown in FIG. 6, the SOM network comprises two layers, i.e., the input layer and competitive layer. The SOM learns to classify feature vectors according to how they are grouped in the feature space, including the distribution and topological structures.

For a feature vector $x = [x_1, x_2, \ldots, x_d]$, the distance to each neuron is measured as $a_i = \|(w_i - x)\|$, where $w_i = [w_{i1}, w_{i2}, \ldots, w_{id}]$, i=1, . . . , M and M is the number of neurons in the SOM. The resulting distance vector $a = [a_1, a_2, \ldots, a_M]$ is then fed into the competitive layer. The competitive transfer function assigns a 1 for output element $a_i$ corresponding to the winning neuron, which is the closest to the input feature vector x. All other output elements in a are 0. The closest neuron is identified as the best matching unit (BMU) of this feature vector.

Furthermore, the BMU and its neighbors on the SOM map are updated by moving towards the input feature vector according to the rule of Kohonen update as:

$$w_i(t+1) = w_i(t) + h_{ci}(t) \cdot [x(t) - w_i(t)] \quad \text{[Equation 6]}$$

where i=1, . . . , M is the index of neurons and t=0, 1, 2, . . . is the training iteration step. Here, $h_{ci}(t)$ is the neighborhood function, which is usually defined as $h_{ci}(t) = h(\|r_c - r_i\|, t)$, where $r_c, r_i \in \Re^2$ are the locations of neuron c and i. This neighborhood function $h_{ci}(t) \to 0$ when $t \to \infty$, and $h_{ci}(t) \to 0$ when $\|r_c - r_i\|$ increases. A Gaussian function can be used for $h_{ci}(t)$ as:

$$h_{ci}(t) = \alpha(t) \cdot \exp\left(-\frac{\|r_c - r_i\|^2}{2[\sigma(t)]^2}\right) \quad \text{[Equation 7]}$$

where $\alpha(t)$ is the learning-rate factor and $\sigma(t)$ is the width of the neighborhood kernel function. Both $\alpha(t)$ and $\sigma(t)$ are monotonically decreasing functions of time.

The SOM arranges high-dimensional vectors of input features in a two-dimensional output space such that similar inputs are mapped onto neighboring SOM regions. Thus, similar patterns of the input data, which represent similar cardiovascular conditions, are preserved within the SOM representation space. The supervised SOM integrates the label information as an additional element in the feature vector during the training phase. The input vector x has two parts, i.e., x=[$x_f$, $x_1$], where $x_f$ is the feature vector and $x_1$ is the corresponding label. The label of each neuron is determined by the majority of its associated input vectors' labels. In the testing phase, the label of best-matching neuron is assigned to an input vector x̃. In some embodiments, the supervised SOM can be utilized as a classification model to identify MI at different locations based on the feature vectors obtained through the spatial embedding of global and local dissimilarity matrices.

In addition, the logistic regression (LR) was utilized to corroborate the SOM classification results. The class membership probability (i.e., between 0 and 1) is:

$$p(x) = \frac{e^{\beta_0 + \beta_1 x_1 + \cdots + \beta_d x_d}}{1 + e^{\beta_0 + \beta_1 x_1 + \cdots + \beta_d x_d}} \quad \text{[Equation 8]}$$

$$= \frac{e^{\beta x'}}{1 + e^{\beta x'}}$$

$$= \frac{1}{1 + e^{-\beta x'}}$$

where x' is the feature vector [1, $x_1$, $x_2$, ..., $x_d$]. Note that each feature vector is associated with a binary-valued outcome. The parameters β are determined with the use of maximum likelihood estimation.

An investigation was performed using 388 VCG recordings (309 MIs and 79 HCs) to evaluate the performance of the above-described methodologies. The VCG signals were digitized at a 1 kHz sampling rate with a 16-bit resolution over a range of ±16.384 mV. Within the 309 MI recordings, there were 47 anterior (AN), 77 anterior-septal (ANSP), 43 anterior-lateral (ANLA), 89 inferior (IN), and 53 inferior-lateral (INLA).

The VCG signals were preprocessed with an FFT bandpass filter (i.e., 1~120 Hz), which removed low-frequency artifacts (e.g., the baseline wonder) and high-frequency noises. In addition, the VCG ensembles were extracted with the use of Poincare sectioning. Then, the ensembles were normalized to the same length of 1000 data points and the averaged VCG cycle was used for warping.

The following experiments were performed to validate the design of the methodology.

1. The influence of embedding dimension: As the embedding dimension increases, the dissimilarities between functional recordings are better preserved in the embedded feature space. However, a higher embedding dimension will increase the model complexity and introduce the "curse of dimensionality" problem. A lower embedding dimension may not fully preserve the distance relationships of functional recordings. In this investigation, a stress cost function was defined to represent the performance of each embedding dimension. Experiments were conducted to investigate how the performance will vary as the embedding dimension increases.

2. The influence of neuron map size: The classification performance of SOM can be influenced by the map size. The larger the map size, the better the performance that can be achieved. However, a large number of neurons will result in "overfitting" problems. In the investigation, experiments were conducted for selecting an optimal neuron map size.

Figure 7:
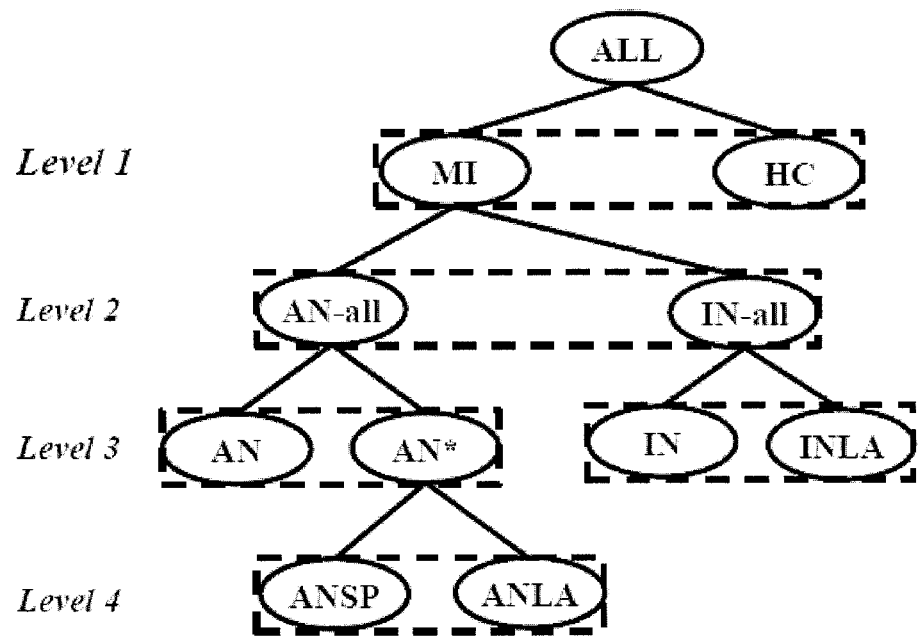
FIG. 7 is a diagram of an embodiment of the structure of hierarchical classification.

3. Hierarchical classification: As shown in FIG. 7, the structure of hierarchical classification comprises four levels: (1) Level 1—HC vs. MI recordings. (2) Level 2—AN-all vs. IN-all. The group of AN-all included MI-anterior, MI-anterior-septal and MI-anterior-lateral. The group of IN-all included MI-inferior and MI-inferior-lateral. (3) Level 3—Within AN-all, MI-anterior-septal and MI-anterior-lateral are combined as AN* to be separated from MI-anterior. Within IN-all, MI-inferior and MI-inferior-lateral are classified. (4) Level 4—MI-anterior-septal vs. MI-anterior-lateral.

Figure 8:
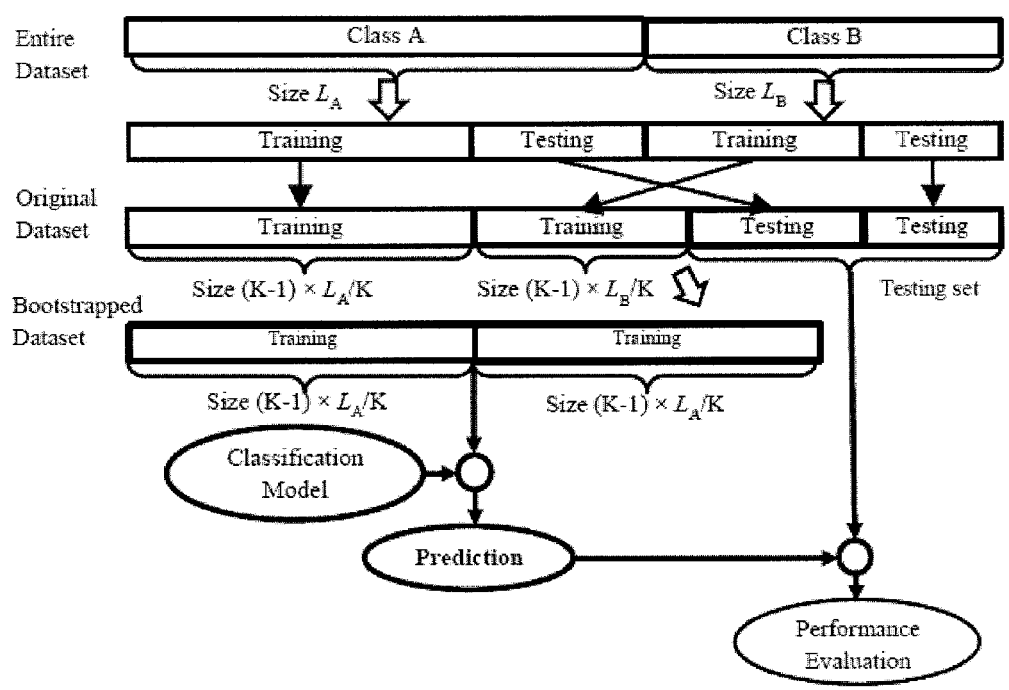
FIG. 8 is a diagram of an embodiment of K-fold cross-validation and bootstrapping methods.

In addition, K-fold cross-validation (i.e., K=4 in the investigation) and random subsampling methods were utilized to surmount the bias and "overfitting" problems in the performance evaluation of SOM classification models. As shown in FIG. 8, the entire dataset was partitioned into K disjoint and equalized folds, in which K−1 folds were used as the training dataset and the remaining 1 fold was for testing. This process is repeated K times until each of the K folds is used once for testing. The true performance estimate is obtained as the average of K performance measures on testing samples. The random subsampling method will further replicate such K-fold cross-validation experiments 100 times by randomly creating the K-fold partitions to obtain the probability distribution of performance statistics.

It may be noted that two classes in the database are imbalanced. For example, there are 79 HC recordings and 309 MI recordings in Level 1. Conventional classification models tend to favor the majority class and overlook the minority class. Therefore, a bootstrapping method was utilized to reconstruct the balanced datasets in the training dataset. As shown in FIG. 8, after the entire dataset was divided into training and testing groups, Class A had (K−1)×$L_A$/K recordings in the training dataset, while Class B had (K−1)×$L_B$/K recordings ($L_A$ and $L_B$ are the number of class A and class B recordings in the entire database, and $L_b$<$L_A$). The minority Class B in the training dataset can be resampled with replacement to increase the size from (K−1)×$L_B$/K to (K−1)×$L_A$/K for constructing a balanced training dataset.

Note that four warping matrices (i.e., global, P, QRS, and T warping) generate a high-dimensional feature space (i.e., 4×10 number of features). This can create the issues of the "curse of dimensionality" for classification models, e.g., increased model parameters, feature correlation, and overfitting problems. Here, a sequential-forward-feature-selection strategy is used to choose an optimal feature subset that is correlated with disease characteristics. In the investigation, the feature size was varied from 1 to 20, and it was found that there is no significant performance improvement when the feature size is greater than 10. In the feature selection, classification models are wrapped into the objective function. Starting from an empty feature subset $S_0$={Ø}, an additional feature $s^+$ is selected when it maximizes the objective function in terms of the predictive accuracy: $\text{argmax}_{s^+ \notin S_k} \Gamma(S_k + s^+)$, where Γ(·) represents the discriminant function. This process is repeated until it reaches the stable period. The step of feature selection cannot only surmount the aforementioned classification complexity and overfitting problems, but also provide faster and more cost-effective models with the optimal feature subset.

In the classification experiments, three performance measures, i.e., correct rate (CR), sensitivity (SEN), and specificity (SPEC), were computed from the testing datasets. The correct rate is the ratio of recordings correctly identified in the testing datasets. Sensitivity measures the proportion of positives which are correctly identified as such, while the specificity measures the proportion of negatives which are correctly identified.

Figure 9:
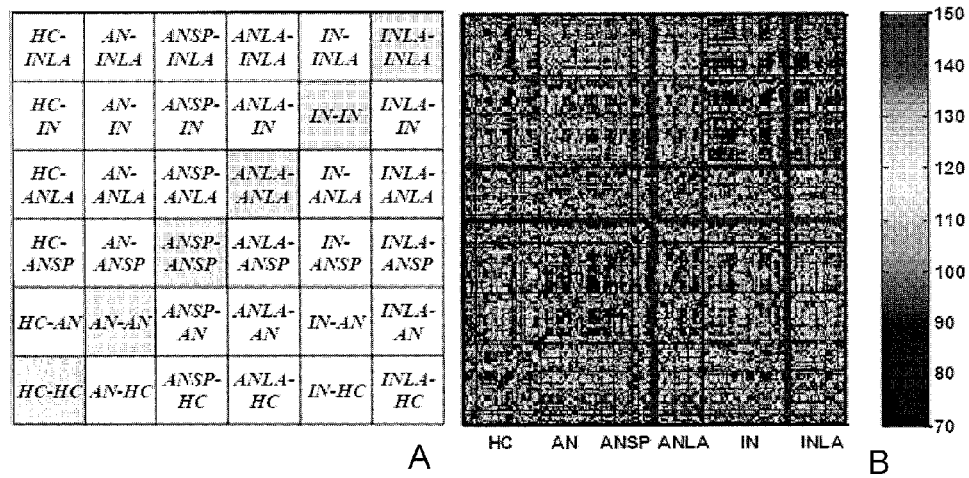
FIG. 9A is a map of labels between pairs of groups in an example dissimilarity matrix.
FIG. 9B is an example color mapping plot of the dissimilarity matrix of FIG. 9A.

As shown in FIG. 9A, the dissimilarity matrix is symmetric with on-diagonal squares representing the in-group dissimilarities and off-diagonal squares representing the dissimilarities across subject groups. In the investigation, there were 309 MIs and 79 HCs. Within the 309 MI recordings, there were 47 anterior (AN), 77 anterior-septal (ANSP), 43 anterior-lateral (ANLA), 89 inferior (IN), and 53 inferior-lateral (INLA).

The dissimilarity matrix was mapped onto a color scale as shown in FIG. 9B. The small distances are in blue colors with gradual transition to the large distances in red colors. The "HC-HC" denotes the distances within HC groups, and "HC-AN" denotes the distances between HC and MI anterior groups. The same nomenclature is used for all other groups. Note that in-group distances are smaller than between-group distances. For example, the on-diagonal squares of HC-HC, AN-AN, ANSP-ANSP, ANLA-ANLA, IN-IN and INLA-INLA are mainly in blue colors, while the off-diagonal squares display more red colors. However, some off-diagonal squares are also in blue colors, e.g., AN-ANSP, IN-INLA. This is because the locations of diseases are spatially close, and the disease-altered patterns of 3-lead VCG are less dissimilar.

The statistical significance of spatiotemporal distances were also tested for different MI locations using the unpaired t-test, F-test, and Kolmogorov-Smirnov (KS) test. Test results are computed from both the global warping matrix (i.e., from the entire VCG loop) and the local warping matrices (i.e., from P, QRS and T segments). The statistically significant results are marked in bold in the tables.

TABLE I

Two Sample T-Test for Testing the Mean of Spatiotemporal Distances at Different MI Locations

| Disease groups | t test results (p-value) | | | |
|---|---|---|---|---|
| | PQRST | P | QRS | T |
| HC-HC vs. HC-AN | 5.36e−4 | 0.02 | 0.09 | 2.99e−4 |
| HC-HC vs. HC-ANSP | 3.79e−06 | 0.02 | 8.17e−5 | 3.67e−06 |
| HC-HC vs. HC-ANLA | 2.35e−05 | 0.002 | 0.02 | 1.46e−05 |
| HC-HC vs. HC-IN | 0.01 | 0.22 | 0.19 | 2.5e−3 |
| HC-HC vs. HC-INLA | 0.70e−2 | 0.08 | 0.16 | 9.84e−4 |
| AN-AN vs. AN-ANSP | 0.05 | 0.43 | 0.08 | 0.04 |
| AN-AN vs. AN-ANLA | 0.20 | 0.25 | 0.71 | 0.14 |
| AN-AN vs. AN-IN | 0.02 | 0.03 | 0.27 | 0.02 |
| AN-AN vs. AN-INLA | 0.06 | 0.03 | 0.19 | 0.20 |
| ANSP-ANSP vs. ANSP-ANLA | 0.99 | 0.54 | 0.56 | 0.81 |
| ANSP-ANSP vs. ANSP-IN | 0.59 | 0.51 | 0.96 | 0.65 |
| ANSP-ANSP vs. ANSP-INLA | 0.98 | 0.45 | 0.96 | 0.70 |
| ANLA-ANLA vs. ANLA-IN | 0.11 | 0.23 | 0.22 | 0.24 |
| ANLA-ANLA vs. ANLA-INLA | 0.27 | 0.20 | 0.11 | 0.78 |
| IN-IN vs. IN-INLA | 0.72 | 0.67 | 0.89 | 0.69 |

First, the central tendency of distances is tested for different MI locations with a 2-sample unpaired t-test. Let $\mu_i$ and $\mu_j$ denote the means of $i^{th}$ and $j^{th}$ groups, the hypotheses of the t-test are:

$$H_0: \mu_i = \mu_j \text{ or } H_1: \mu_i \neq \mu_j$$

For each pair of groups, the t-test statistic is $$t_{unpaired} = (\mu_i - \mu_j)/\sqrt{(s_i^2/n_i) + (s_j^2/n_j)}$$

where $s_i^2$ is the sample variance of the $i^{th}$ group, and $n_i$ and $n_j$ are the number of independent observations in the corresponding group. Further, the p-value is Prob $(|t_{n_i+n_j-2}| >^t_{unpaired})$Prob$(|t_{n_i+n_j-2}| >^t_{unpaired})$. If the p-value is less than the significant level (i.e., $\alpha = 0.05$), the null hypothesis $H_0$ will be rejected and the mean values of two groups are declared to be different at a significant level of 0.05. As shown in Table I, the average distances within the HC group are significantly different from the MI groups (i.e., AN, ANSP, ANLA, IN, and INLA) in both PQRST and T warping. In addition, the AN and IN groups are statistically significant in the PQRST and T warping.

Table II shows that the variances within the HC group are significantly different from ANSP and IN, as shown in PQRST and T warping. Also, the AN group is significantly different from the ANSP and INLA (i.e., from the PQRST, QRS, and T warping). Furthermore, the INLA group is significantly different from ANLA and IN (i.e., from the PQRST, QRS, and T warping).

TABLE II

Two Sample F-Test for Testing the Variances of Spatiotemporal Distances at Different MI Locations

| Disease groups | F test results (p-value) | | | |
|---|---|---|---|---|
| | PQRST | P | QRS | T |
| HC-HC vs. HC-AN | 0.56 | 0.98 | 0.73 | 0.56 |
| HC-HC vs. HC-ANSP | 0.13e−2 | 0.03 | 6.06e−7 | 6.1e−3 |
| HC-HC vs. HC-ANLA | 0.47 | 0.21 | 0.88 | 0.19 |
| HC-HC vs. HC-IN | 0.04 | 0.94 | 0.02 | 0.05 |
| HC-HC vs. HC-INLA | 0.82 | 0.31 | 0.26 | 0.78 |
| AN-AN vs. AN-ANSP | 0.01 | 0.01 | 0.01 | 0.01 |
| AN-AN vs. AN-ANLA | 0.73 | 0.44 | 0.27 | 0.12 |
| AN-AN vs. AN-IN | 0.42 | 0.60 | 0.93 | 0.24 |
| AN-AN vs. AN-INLA | 0.09 | 0.72 | 0.04 | 0.25 |
| ANSP-ANSP vs. ANSP-ANLA | 0.31 | 0.59 | 0.14 | 0.80 |
| ANSP-ANSP vs. ANSP-IN | 0.56 | 0.28 | 0.66 | 0.48 |
| ANSP-ANSP vs. ANSP-INLA | 0.15 | 0.38 | 0.32 | 0.07 |
| ANLA-ANLA vs. ANLA-IN | 0.65 | 0.67 | 0.23 | 0.59 |
| ANLA-ANLA vs. ANLA-INLA | 0.03 | 0.53 | 0.13 | 0.11 |
| IN-IN vs. IN-INLA | 0.04 | 0.49 | 0.02 | 0.05 |

TABLE III

Two Sample KS-Test for Testing the CDFs of Spatiotemporal Distances at Different MI Locations

| Disease groups | KS test results (p-value) | | | |
|---|---|---|---|---|
| | PQRST | P | QRS | T |
| HC-HC vs. HC-AN | 0.76e−3 | 0.02 | 0.26 | 1.30e−3 |
| HC-HC vs. HC-ANSP | 0.14e−3 | 0.06 | 5.50e−03 | 3.04e−04 |
| HC-HC VS. HC-ANLA | 0.23e−3 | 0.01 | 0.07 | 4.64e−04 |
| HC-HC vs. HC-IN | 0.13 | 0.72 | 0.95 | 0.04 |
| HC-HC vs. HC-INLA | 0.02 | 0.50 | 0.26 | 7.40e−3 |
| AN-AN vs. AN-ANSP | 0.83 | 0.99 | 0.77 | 0.84 |
| AN-AN vs. AN-ANLA | 0.99 | 0.96 | 0.99 | 0.96 |
| AN-AN vs. AN-IN | 0.23 | 0.30 | 0.66 | 0.35 |
| AN-AN vs. AN-INLA | 0.27 | 0.22 | 0.18 | 0.76 |
| ANSP-ANSP vs. ANSP-ANLA | 0.99 | 0.99 | 0.97 | 0.99 |
| ANSP-ANSP vs. ANSP-IN | 0.65 | 0.79 | 0.80 | 0.82 |
| ANSP-ANSP vs. ANSP-INLA | 0.66 | 0.70 | 0.52 | 0.95 |
| ANLA-ANLA vs. ANLA-IN | 0.36 | 0.70 | 0.98 | 0.49 |
| ANLA-ANLA vs. NLA-INLA | 0.25 | 0.38 | 0.43 | 0.80 |
| IN-IN vs. IN-INLA | 0.99 | 0.99 | 0.78 | 0.99 |

As shown in Table III, five significant groups are highlighted in bold. It may be noted that the cumulative distribution function of the HC group is significantly different than the AN, ANSP, ANLA, IN, and INLA groups.

The results of three hypothesis tests show that the spatiotemporal distances within the HC group are significantly different from myocardial infarctions at different locations.

Furthermore, MI anterior (AN) shows significant spatiotemporal differences in terms of mean and variance from MI inferior (IN). In addition, there are significant differences within the group of AN and IN subjects, e.g., the IN group is different from INLA in the variances of spatiotemporal distances. It may also be noted that PQRST and T warping yield more significant statistical testing results than QRS warping and P warping. The QRS warping yields more significant differences in the variances of spatiotemporal distances for the AN and IN groups. In other words, this agrees with the aforementioned MI-induced ECG changes in the QRS, ST, and T segments because the MIs usually take place in the ventricles and impact the ventricular depolarization and repolarization. In summary, the results of three statistical tests show that space-time cardiac electrical activities are significantly altered by the MIs at different locations.

Figure 10:
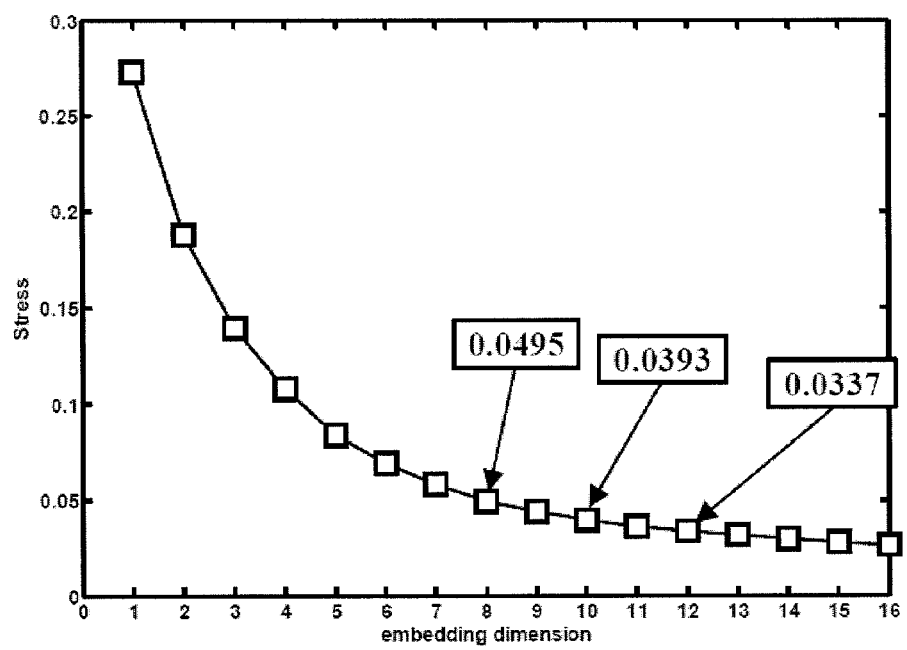
FIG. 10 is a graph that shows stress values for embedding dimensions from 1 to 16.

The Kruskal's stress metric can be used to optimally select the embedding dimension. The stress is calculated as $$\text{stress} = \sqrt{\frac{\sum_{i=1}^{N}\sum_{j=1}^{N}(\delta_{ij} - d_{ij})2}{\sum_{i=1}^{N}\sum_{j=1}^{N}d_{ij}^2}}$$ [Equation 9]

where $d_{ij}$ is the distance between feature vectors $x_i$ and $x_j$, and $d_{ij}$ is the dissimilarity matrix $\Delta$ measured from functional recordings. In this present study, the embedding dimension is varied from 1 to 16 and the stress values are as shown in FIG. 10. The decreasing trend of stress values becomes stable when the embedding dimension reaches 8, 9 and higher. For eight-dimensional embedding, the stress value is around 0.0495. The stress value is 0.0393 for the ten-dimensional embedding. As shown in FIG. 10, the stress is 0.0337 when the embedding dimension is increased to 12. A small stress value is sufficient to reconstruct the dissimilarities in the dissimilarity matrix. Thus, 10 was selected as the embedding dimension in the investigation.

Figure 11:
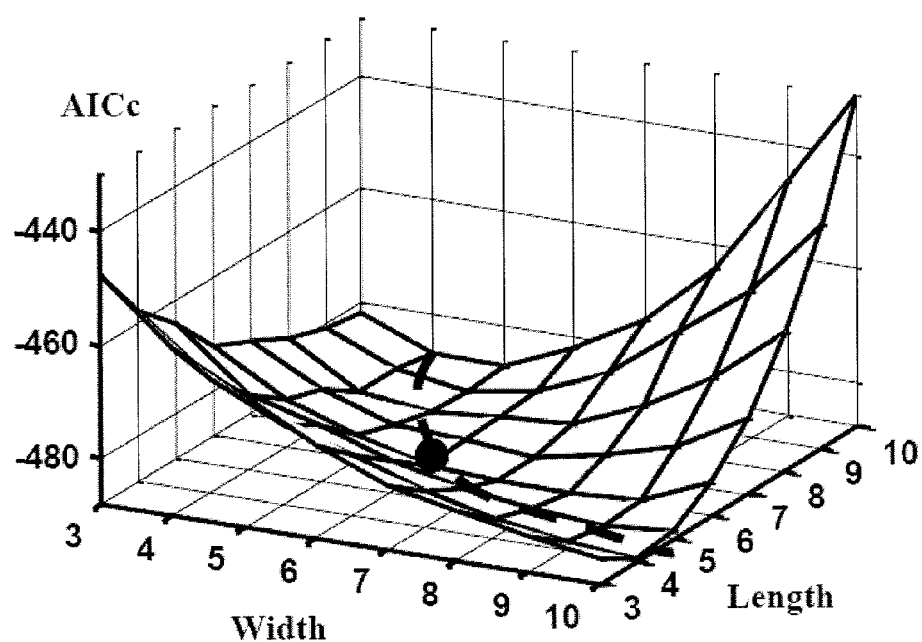
FIG. 11 is a graph that shows the response surface of AICc for different SOM map sizes.

The Akaike information criterion (AICc) for the selection of an optimal SOM model is defined as:

$$AICc = 2k + Nln(QE) + \frac{2k(k+1)}{N-k-1}$$ [Equation 10]

where k is the number of neurons in the SOM model, and N is the number of recordings. The quantization error (QE) is defined as:

$$QE = \frac{1}{N}\sum_{n=1}^{N}\|x_n - w_{c(n)}\|,$$

where $x_n$ is the input feature vector and $w_{c(n)}$ is the weighting vector of the best matching neuron for the input feature vector $x_n$. It may be noted that 2k represents the penalty of model complexity, and Nln(QE) represents model performance. The term $$\frac{2k(k+1)}{N-k-1}$$

is added to adjust the penalty of model complexity (i.e., 2k) on the basis of sample size N. In other words, a balance between model performance and complexity will be achieved by minimizing the AICc values. As shown in FIG. 11, the response surface of AICc has higher amplitudes at both small and large map sizes. An optimal SOM map size of (6, 6) (i.e., the dot in FIG. 11) is selected for further visualization of SOM structure and identification of disease properties.

Figure 12:
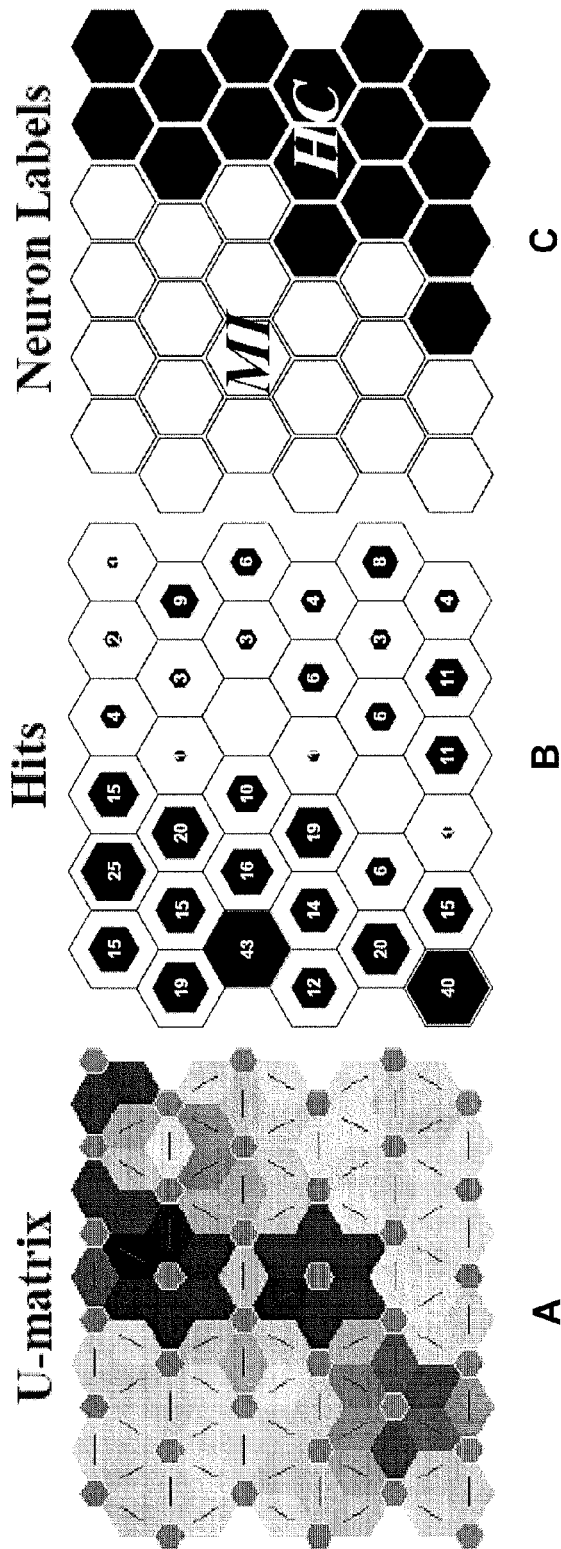
FIG. 12A is a SOM U-matrix for particular neuron distances.
FIG. 12B is a plot of SOM sample hits.
FIG. 12C are SOM neuron labels of HD and MI subjects.

FIG. 12 shows the visualization of SOM structures for classifying MI and HC recordings at Level 1 using embedded features from the PQRST dissimilarity matrix. As shown in FIG. 12A, the distances between neurons in the SOM are represented in a U-matrix. It may be noted that the distances in left and right portions are in light yellow colors and separated by the darker colors in the middle. The U-matrix indicates that features vectors are organized into 2 clusters according to the self-organizing SOM structure. FIGS. 12B and 12C show the plots of SOM sample hits and neuron labels. It may be noted that the neurons in the left portion of the SOM map (colored as light red) represent MI and the right portion (colored as deep blue) represent HC. The two groups are separated effectively in the SOM map.

Table IV shows the experimental results for the identification of MI locations using hierarchical classification. A total of 40 features were extracted from the PQRST, P, QRS, and T warping. Hence, a subset of features (i.e., 10 out of 40 features) was optimally selected to reduce the model complexity and prevent overfitting. The feature selection strategy evaluates the covariance function and identifies highly correlated features. Due to the multi-class hierarchical structure, the feature selection is performed at each level. In other words, features selected in Level 1 may not still be effective for other levels. This is because when separating HC vs. MI in Level 1, all the MI sub-groups are treated equally as one group. However, Levels 2-4 are aimed at separating the MI sub-groups. Therefore, the features selected in each level are dependent on the objective function in the structure of hierarchical classification.

TABLE IV

Hierarchical Classification Results of Selected Features

| Level | Group | Model | CR (%) | SEN (%) | SPEC (%) |
|---|---|---|---|---|---|
| 1 | HC vs. MI | SOM | 95.1 (±0.4) | 94.9 (±0.5) | 95.7 (±0.7) |
|  |  | LR | 91.4 (±0.2) | 92.5 (±0.2) | 86.8 (±0.4) |
| 2 | AN-all vs. IN-all | SOM | 95.8 (±0.4) | 95.7 (±0.5) | 95.8 (±0.6) |
|  |  | LR | 94.3 (±0.2) | 93.8 (±0.3) | 94.8 (±0.4) |
| 3 | AN vs. AN* | SOM | 89.5 (±0.8) | 89.0 (±1.1) | 90.7 (±1.7) |
|  |  | LR | 73.1 (±0.8) | 77.7 (±1.1) | 61.5 (±1.2) |
|  | IN vs. INLA | SOM | 91.4 (±0.7) | 87.9 (±1.4) | 93.5 (±1.0) |
|  |  | LR | 85.1 (±0.7) | 85.7 (±1.0) | 84.7 (±0.9) |
| 4 | ANSP vs. ANLA | SOM | 96.1 (±0.7) | 95.8 (±1.0) | 96.3 (±1.0) |
|  |  | LR | 86.7 (±0.7) | 84.1 (±1.0) | 88.1 (±1.0) |

In addition, because of the limited sample size, performance metrics in each level are not based on the classification results obtained from the preceding levels, but on the whole study population in each level. For example, the entire MI recordings are used in Level 2 to separate AN-all vs. IN-all, as opposed to the correctly identified MIs from the preceding Level 1.

At Level 1 (HC vs. MI), the SOM model yields the averaged performances of CR-95.1%, SEN-94.9%, and SPEC-95.7%. Also, the Logistic Regression (LR) model achieves the results of CR-91.4%, SEN-92.5%, and SPEC- 86.8%. Both SOM and LR models show similar results, indicating that warping features are effective in terms of separating HCs and MIs.

At Level 2 (AN-all vs. IN-all), the performances are much better for both SOM and LR models. The average correct rates are 95.8% for the SOM model and 94.3% for the LR model. It is worth mentioning that anterior MIs are located at the front of the heart, and inferior MIs are closer to the bottom. The results show that distinct differences in spatial locations of diseases also lead to big variations in the exhibited signatures (i.e., 3-lead VCGs).

At Level 3, the locations of lesions are spatially closer. The disease-altered patterns of 3-lead VCGs are less dissimilar. Therefore, the performances of both models are worse than the previous two levels. As shown in Table IV, the SOM model only achieved a correct rate of 89.5% for AN vs. AN*. However, the LR model has a correct rate of 73.1%. This may be due to the fact that AN* includes AN-septal and AN-lateral, which are in different sides of AN. When AN-septal and AN-lateral are combined in a single group of AN*, this poses significant challenges for the linear-form model to separate two different kinds of patterns in AN* from AN.

However, the SOM model yields the averaged performances of CR-91.4%, SEN-87.9% and SPEC-93.5% for IN vs. INLA at Level 3. The LR model yields the results of CR-85.1%, SEN-85.7% and SPEC-84.7%. Note that the population is homogeneous in the groups of either IN or INLA, which is different from the inhomogeneous group of AN*. In addition, the SOM model is better able to handle the nonlinear relationships in the data than the LR model.

At Level 4 (ANSP vs. ANLA), the population in ANSP or ANLA is homogeneous. The correct rates are 96.1% for the SOM model and 86.7% for the LR model because of the spatial closeness of lesions. In the classification experiments, it may be noted that the LR model is used to corroborate the results of the SOM model. Both SOM and LR models achieved similar performances.

Figure 13:
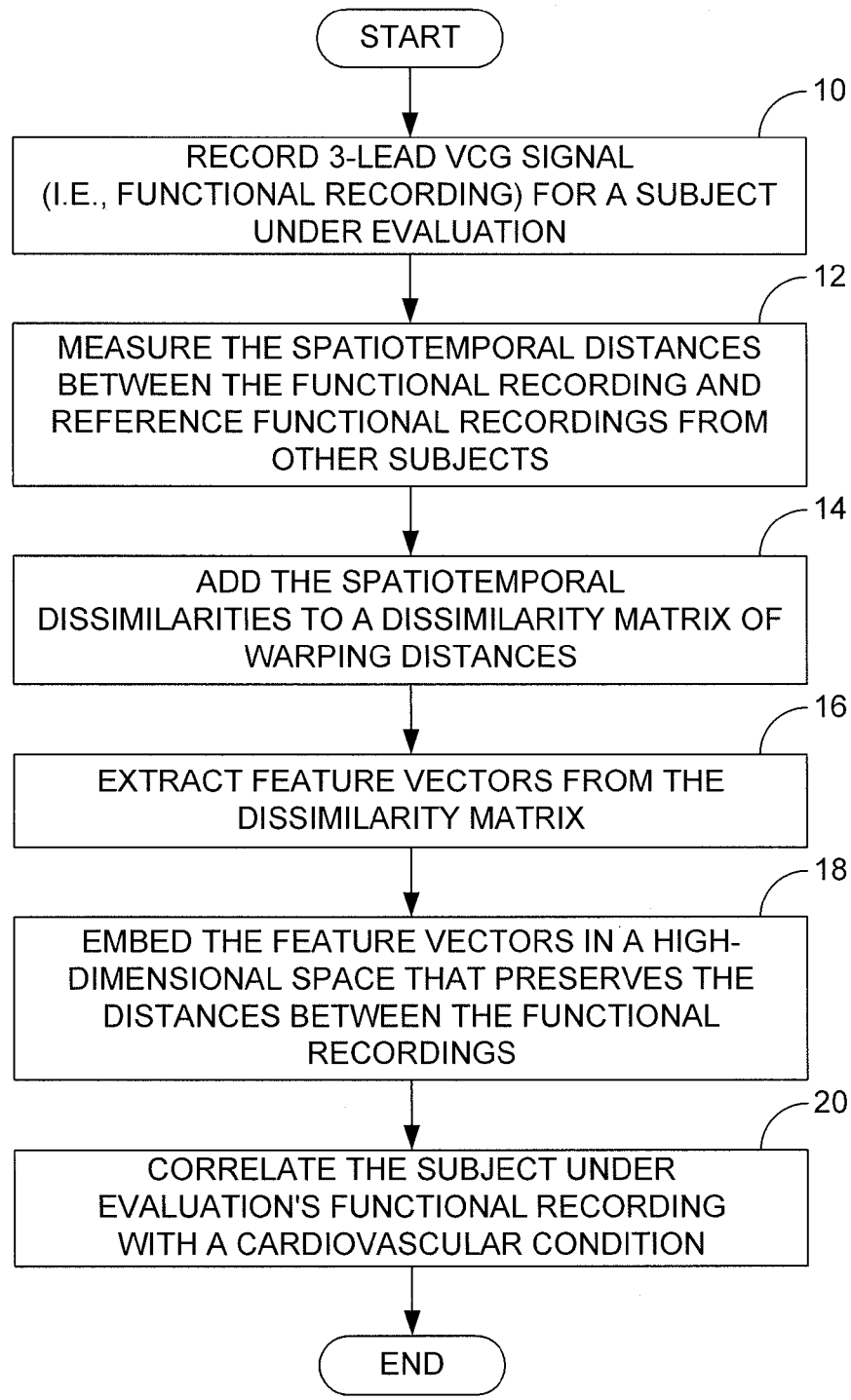
FIG. 13 is a flow diagram that illustrates an embodiment of a method for diagnosing a cardiovascular condition.

Using the above-described methodologies, cardiovascular conditions, such as MI, can be diagnosed. FIG. 13 illustrates an example method for diagnosing a cardiovascular condition. In this figure, it is assumed that a subject under evaluation (e.g., a patient) is to be diagnosed. Beginning with block 10 of FIG. 13, 3-lead VCG signals (i.e., functional recordings) are recorded for the subject under evaluation. In some embodiments, the signals can be recorded by placing electrodes on the subject's skin surface in front of the heart (on the chest), behind the heart (on the back), to either side of the heart (on the sides of the torso), above the heart (e.g., on the neck), and below the heart (e.g., on the hip). With these six electrodes, three signals or "leads" can be recorded that can be combined to generate the VCG signals. In some embodiments, the VCG signals can be global functional recordings, in which case they include the P wave, QRS complex, and the T wave. In other embodiments, the VCG signals can alternatively or additionally include discrete segments of the global functional recordings individually pertaining to the P, QRS, and T loops.

Once the functional recording has been obtained, spatiotemporal distances (dissimilarities) between the functional recording and reference functional recordings previously obtained for other subjects can be measured, as indicated in block 12. In some embodiments, the reference functional recordings can be stored in a large database of functional recordings captured for many subjects, including both healthy and diseased subjects, whose cardiovascular conditions are known. In this manner, space-time cardiac electrical activity of the subject under evaluation can be compared with that of many others in an effort to categorize the cardiac function of the subject under evaluation. As described above, spatiotemporal dissimilarities can, in some embodiments, be determined using a dynamic spatiotemporal warping algorithm. Notably, spatiotemporal dissimilarities can be determined for the global functional recordings and/or for one or more local functional recordings relating to one or more of the P, QRS, and T loops.

The measured spatiotemporal dissimilarities can be added to a dissimilarity matrix of warping distances (block 14) that identifies the spatiotemporal dissimilarity between each subject's functional recording and the functional recording of each other subject from the database. FIG. 5A, which was discussed above, presents a simple example of such a matrix. Adding the subject under evaluation's spatiotemporal dissimilarities results in the addition of a further row and column to the matrix. In cases in which dissimilarities for both the global and one or more local functional recordings were measured, the dissimilarities can be independently added to separate dissimilarity matrices (a global dissimilarity matrix, a P loop dissimilarity matrix, etc.).

Next, feature vectors can be extracted from the dissimilarity matrix or matrices, as indicated in block 16. As described above, the feature vectors can be extracted using a feature embedding algorithm. Using the feature embedding algorithm, the feature vectors can be embedded in a high-dimensional space to form a network that preserves the warping distances between all of the functional recordings, as indicated in block 18. FIG. 5B, which was discussed above, presents a simple example of a 3-D network that results from such embedding. In the network, each node represents a functional recording of a subject and the lines extending between nodes define the relationships between the nodes.

At this point, the functional recording (node) of the subject under evaluation can be correlated with a particular cardiovascular condition, as indicated in block 20. If multiple dissimilarity matrices and multiple networks were generated, this correlation can be performed for each network. As described above, a classification model can be used for this purpose. For example, a SOM can be used to correlate the subject's functional recording with functional recordings of patients having a particular cardiovascular condition. For example, if through the mapping the subject under evaluation's functional recording it is determined that the functional recording is located within the space of the network at which the functional recordings of anterior MI subjects are clustered, it is likely that the subject under evaluation also has an anterior MI. Alternatively, if the subject under evaluation's functional recording is located within the space of the network at which the functional recordings of healthy subjects are clustered, it is likely that the subject under evaluation is also healthy. In this manner, the cardiovascular condition of the subject under evaluation can be determined by the spatial location of his or her functional recording relative to those of other subjects whose cardiovascular conditions are already known. Once this determination has been made, it can be output to a physician, who can use it as a resource in making a diagnosis for the subject under evaluation.

Figure 14:
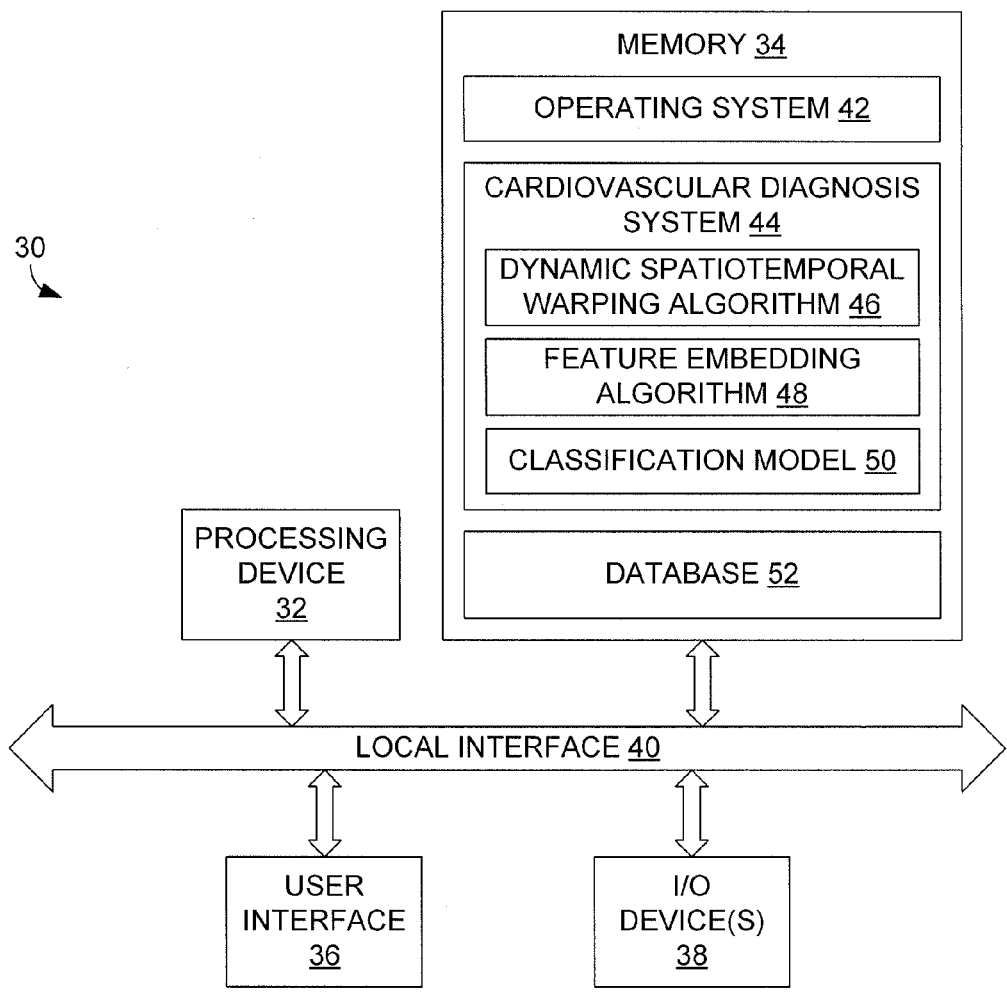
FIG. 14 is a block diagram of an embodiment of a computing device that can be used in the method described in relation to FIG. 12.

FIG. 14 illustrates an example configuration for a computing device 30 that can be used to facilitate the methodologies described above, including the method of FIG. 13. The computing device 30 can take many different forms. For example, the computing device 30 can be configured as a desktop computer, notebook computer, tablet computer, or any other computing device that has adequate computing and display capabilities.

In the example of FIG. 14, the computing device 30 includes a processing device 32, memory 34, a user interface 36, and at least one I/O device 38, each of which is connected to a local interface 40. The processing device 32 can include a central processing unit (CPU) or a semiconductor-based microprocessor (in the form of a microchip). The memory 34 includes any one of or a combination of volatile memory elements (e.g., RAM) and nonvolatile memory elements (e.g., hard disk, ROM, Flash, etc.). The user interface 36 comprises the components with which a user interacts with the computing device 30, such as a keyboard, keypad, and a display screen, and the I/O devices 38 are adapted to facilitate communications with other devices.

The memory 34 (a non-transitory computer-readable medium) comprises programs (logic) including an operating system 42 and a cardiovascular diagnosis system 44. In the example of FIG. 14, the cardiovascular diagnosis system 44 includes a dynamic spatiotemporal warping algorithm 46, a feature embedding algorithm 48, and a classification model 50, the functionality of each having been described above. In addition, the memory 34 comprises a database 52 that can include functional recordings of multiple subjects, dissimilarity matrices, and high-dimensional networks of functional recordings.

The invention claimed is:

1. A method for diagnosing a cardiovascular condition, the method comprising:
   recording a vectorcardiogram for a subject under evaluation to obtain a functional recording;
   comparing the functional recording with functional recordings of other subjects by:
      measuring spatiotemporal distances between the functional recordings,
      creating a dissimilarity matrix of the measured spatiotemporal distances,
      extracting feature vectors from the dissimilarity matrix, and
      embedding the feature vectors in a high-dimensional space that preserves the distances between the functional recordings; and
   diagnosing the subject under evaluation based upon the comparison.

2. The method of claim 1, wherein measuring spatiotemporal distances comprises measuring the spatiotemporal distances using a spatiotemporal warping algorithm.

3. The method of claim 2, wherein the spatiotemporal warping algorithm is configured to determine a time-normalized spatial distance between the functional recordings.

4. The method of claim 1, wherein the extracting and embedding comprise extracting and embedding using a feature embedding algorithm.

5. The method of claim 1, wherein diagnosing the subject comprises correlating the subject under evaluation's functional recording with those of the other subjects.

6. The method of claim 5, wherein correlating comprises correlating the subject under evaluation's functional recording with those of the other subjects using a classification model.

7. The method of claim 6, wherein the classification model is a self-organizing map configured to correlate feature vectors with spatial locations of particular cardiovascular conditions by representing the high-dimensional space as a low-dimensional space.

8. A non-transitory computer-readable medium that stores a cardiovascular diagnosis system, the system comprising:
   logic configured to compare a functional recording obtained from a vectorcardiogram of a subject under evaluation with functional recordings of other subjects by:
      measuring spatiotemporal distances between the functional recordings,
      creating a dissimilarity matrix of the measured spatiotemporal distances,
      extracting feature vectors from the dissimilarity matrix, and
      embedding the feature vectors in a high-dimensional space that preserves the distances between the functional recordings; and
   logic configured to diagnose the subject under evaluation based upon the comparison.

9. The computer-readable medium of claim 8, wherein the logic configured to measure spatiotemporal distances comprises a spatiotemporal warping algorithm.

10. The computer-readable medium of claim 9, wherein the spatiotemporal warping algorithm is configured to determine a time-normalized spatial distance between the functional recordings.

11. The computer-readable medium of claim 8, wherein the logic configured to extract and embed comprises a feature embedding algorithm.

12. The computer-readable medium of claim 8, wherein the logic configured to diagnose the subject comprises logic configured to correlate the subject under evaluation's functional recording with those of the other subjects.

13. The computer-readable medium of claim 12, wherein the logic configured to correlate comprises a classification model.

14. The computer-readable medium of claim 13, wherein the classification model is a self-organizing map configured to correlate the feature vectors with spatial locations of particular cardiovascular conditions by representing the high-dimensional space as a low-dimensional space.

15. A computing device comprising:
   a processing device; and
   memory that stores a cardiovascular diagnosis system, the system including:
      logic configured to compare a functional recording obtained from a vectorcardiogram of a subject under evaluation with functional recordings of other subjects by:
         measuring spatiotemporal distances between the functional recordings,
         creating a dissimilarity matrix of the measured spatiotemporal distances,
         extracting feature vectors from the dissimilarity matrix, and
         embedding the feature vectors in a high-dimensional space that preserves the distances between the functional recordings; and
      logic configured to diagnose the subject under evaluation based upon the comparison.

16. The computing device of claim 15, wherein measuring spatiotemporal distances comprises measuring the spatiotemporal distances using a spatiotemporal warping algorithm configured to determine a time-normalized spatial distance between the functional recordings.

17. The computing device of claim 15, wherein the extracting and embedding comprise extracting and embedding using a feature embedding algorithm.

18. The computing device of claim 15, wherein the logic configured to diagnose the subject comprises logic configured to correlate the subject under evaluation's functional recording with those of the other subjects.

19. The computing device of claim 18, wherein the logic configured to correlate comprises logic configured to correlate the subject under evaluation's functional recording with those of the other subjects using a classification model.

20. The computing device of claim 19, wherein the classification model is a self-organizing map configured to correlate the feature vectors with spatial locations of particular cardiovascular conditions by representing the high-dimensional space as a low-dimensional space.

* * * * *